(12) United States Patent
Yoshimasa

(10) Patent No.: US 6,700,035 B2
(45) Date of Patent: Mar. 2, 2004

(54) ABSORBENT ARTICLE

(75) Inventor: Wataru Yoshimasa, Kagawa (JP)

(73) Assignee: Uni-Charm Corporation, Kawanoe (JP)

( * ) Notice: Subject to any disclaimer, the term of this patent is extended or adjusted under 35 U.S.C. 154(b) by 228 days.

(21) Appl. No.: 09/854,702

(22) Filed: May 14, 2001

(65) Prior Publication Data
US 2002/0010448 A1 Jan. 24, 2002

(30) Foreign Application Priority Data
May 31, 2000 (JP) .................... 2000-161418

(51) Int. Cl.$^7$ ............................................. A61F 13/15
(52) U.S. Cl. .................................................. 604/378
(58) Field of Search ............................ 604/378, 372, 604/367

(56) References Cited

U.S. PATENT DOCUMENTS

| | | | | |
|---|---|---|---|---|
| 4,600,458 A | | 7/1986 | Kramer et al. ............... | 156/199 |
| 5,143,779 A | * | 9/1992 | Newkirk et al. ............. | 428/218 |
| 5,334,177 A | | 8/1994 | Cohen ......................... | 604/378 |
| 5,356,405 A | | 10/1994 | Thompson et al. .......... | 604/384 |
| 5,591,149 A | * | 1/1997 | Cree et al. ................... | 604/378 |
| 5,658,268 A | * | 8/1997 | Johns et al. ................. | 604/361 |
| 5,821,179 A | | 10/1998 | Masaki et al. ............... | 442/375 |
| 5,885,267 A | * | 3/1999 | Mishima et al. ............. | 604/378 |
| 5,951,535 A | | 9/1999 | Fujiwara et al. ............. | 604/384 |
| 6,245,961 B1 | * | 6/2001 | Roxendal et al. ........... | 604/367 |
| 6,417,427 B1 | * | 7/2002 | Roxendal et al. ........... | 604/378 |
| 6,420,626 B1 | * | 7/2002 | Erspamer et al. ........... | 604/378 |

FOREIGN PATENT DOCUMENTS

| | | | |
|---|---|---|---|
| EP | 0596532 | 5/1994 | ........... A61F/13/46 |
| EP | 0852268 | 7/1998 | ........... D01F/6/46 |
| JP | 05-200065 | 8/1993 | |
| JP | 10-512168 | 11/1998 | |
| WO | WO96/21682 | 11/1998 | |

* cited by examiner

Primary Examiner—Weilun Lo
Assistant Examiner—Catharine L Anderson
(74) Attorney, Agent, or Firm—Darby & Darby (57) ABSTRACT

There is provided an absorbent article including: a support sheet; a liquid-absorbing layer disposed on the support sheet; and a liquid-permeable surface sheet covering the liquid-receiving face of the liquid-absorbing layer. Between the liquid-absorbing layer and the surface sheet, there is provided a liquid-permeable layer of crimped fibers which remain in a crimped state in a natural state without any external force. The crimped fiber layer is formed by interconnecting the crimped fibers to leave voids therebetween.

5 Claims, 6 Drawing Sheets

ABSORBENT ARTICLE

BACKGROUND OF THE INVENTION

1. Field of the Invention

The present invention relates to an absorbent article such as a sanitary napkin, a panti-liner or a disposable diaper and, more particularly, to an absorbent article which has little pressure but excellent fitness.

2. Related Art

In recent years, there have been many absorbent articles such as sanitary napkins, panti-liners, incontinence pads or disposable diapers for absorbing a discharged substance. Each of these absorbent articles is generally constructed to include: a liquid-permeable surface sheet to be directed to the wearer; a liquid-impermeable back sheet; and a liquid-absorbing layer sandwiched between the surface sheet and the back sheet. The surface sheet is brought into direct contact with the wearer's skin so that it is preferred to provide a softer touch feel. Especially where the absorbent article is exemplified by the sanitary napkin, the surface sheet is a portion to receive the discharged liquid such as the menstrual blood directly from the vaginal opening. Therefore, the surface sheet has to enhance the contact with the vaginal opening thereby to prevent leakage of the liquid inbetween.

However, the shape of the portion near the vaginal opening of a woman is complicated and has large individual differences so that the sanitary napkin is difficult to be formed in advance into such a specific shape as to enhance the contact.

In a sanitary napkin developed in the prior art, therefore, a fine pattern of roughness is formed on the surface sheet, for example, as disclosed in Japanese Patent Laid-Open No. 200065/1993. In the surface sheet thus formed with the roughness pattern, however, the undulations are substantially identical in a substantially constant bulk so that the enhancement of the contact between the surface sheet and the vaginal opening is restricted.

As disclosed in International Patent Publication No. 512168/1998, on the other hand, there is a structure using a foam in an absorbent core. Generally speaking, however, the foam has a relatively high strength (in the compressive deflection) and a high repulsion so that the stimulation (e.g., resistance or load) to the wearer's skin becomes increased thereby to raise a problem that a physical disorder is easily given to the wearer.

SUMMARY OF THE INVENTION

The present invention has an object to provide an absorbent article which is enabled to deform according to the shape of the private part of a wearer to thereby prevent leakage of a discharged liquid.

Another object of the invention is to provide an absorbent article which is so soft to the private part of a wearer as to contact gently with the skin.

According to an aspect of the invention, there is provided an absorbent article comprising: a support sheet; a liquid-absorbing layer disposed on the support sheet; and a liquid-permeable surface sheet covering the liquid-receiving face of the liquid-absorbing layer, wherein between the liquid-absorbing layer and the surface sheet, there is provided a liquid-permeable layer of crimped fibers which remain in a crimped state in a natural state without any external force, the crimped fiber layer being formed by interconnecting the crimped fibers to leave voids therebetween.

According to another aspect of the invention, there is provided an absorbent article comprising: a support sheet; a liquid-absorbing layer disposed on the support sheet; and a liquid-permeable surface sheet covering the liquid-receiving face of the liquid-absorbing layer, wherein the liquid-absorbing layer is formed of: a layer of crimped fibers which remain in a crimped state in a natural state without any external force, the crimped fiber layer being formed by interconnecting the crimped fibers to leave voids therebetween; and a liquid-absorbent material. In this structure, it is preferred that the liquid-absorbent material comprises at least one of liquid-absorbing fibers and an absorbent resin, and that the liquid-absorbent material is buried in the voids of the crimped fiber layer.

For example, the crimped fiber layer may be prepared by laminating a plurality of resin layers of different MFRs (melt flow rates) into a laminate film and by splitting the laminate film into a network.

Alternatively, the crimped fiber layer may be prepared by joining the crimped fibers at their intersections into a network.

Preferably, the crimped fibers are given such a sectional shape as has a larger width of 10 to 500 microns than a thickness of 10 to 100 microns and as has the maximum of a crimping external diameter of 0.3 to 20 mm in a free state without any external force.

Preferably, the crimped fiber layer has a shrinking tension of 50 mN or less for a width of 25 mm when the crimped fiber layer has a thickness of 3 to 30 mm and a tensile strain of 50% is applied in the longitudinal direction of the absorbent article only to the crimped fiber layer.

Preferably, a pushing load necessary for pushing the surface sheet by 5 mm is 150 mN or less for an area of 10 mm Φ for the laminate of the liquid-absorbing layer, the liquid-permeable layer and the surface sheet. In this construction, it is preferred that the bulk recovery percentage of the pushed portion when the pushing force for 5 mm is released is no less than 40% and no more than 100%.

The liquid-permeable layer in the absorbent article of the invention is an aggregate of crimped fibers (or crimped filaments). If these crimped fibers are arranged to extend generally along the liquid-receiving face, the crimping external diameter thereof is directed generally in the height direction from the liquid-receiving face. The force necessary for tensing the crimped fibers in the fiber extending directions is so low that the restoring force (or the spring-back force) when the absorbent article is curved to the body shape is low. On the other hand, the crimped fibers have a remarkably low elastic modulus in the height direction from the liquid-receiving face, along which the crimping external diameter thereof is directed, so that the surface sheet can be easily deformed to conform to the shape of the private part of a wearer (e.g., the vaginal opening and therearound). Moreover, the elastic reaction for the deformation is so low that the pressure on the private part is accordingly low. Therefore, the absorbent article is excellent in the wearing feel and in the sealing performance.

Moreover, the crimped fibers have a function to guide the body liquid along the crimped portions from the surface sheet to the liquid-absorbing layer so that the body liquid having passed through the surface sheet can be quickly introduced into the liquid-absorbing layer.

DESCRIPTION OF THE PREFERRED EMBODIMENTS

The invention will be described with reference to the accompanying drawings.

As used herein, the term "absorbent article" refers to devices which absorb and contain body liquids, and more specifically, refers to devices which are placed against the skin of a wearer to absorb and contain the various liquids discharged from the body. Examples of absorbent articles include sanitary napkins, panti-liners, diapers, incontinence pads, and the like.

Figure 1:
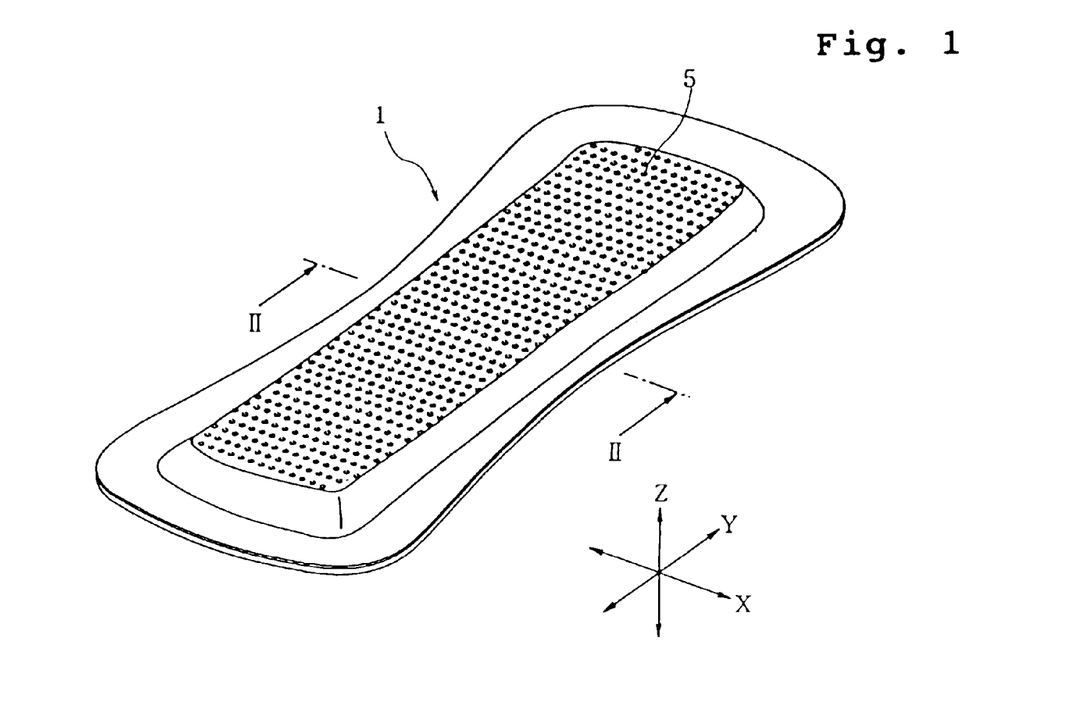
FIG. 1 is a perspective view showing a sanitary napkin as an absorbent article according to an embodiment of the invention.
Figure 2:
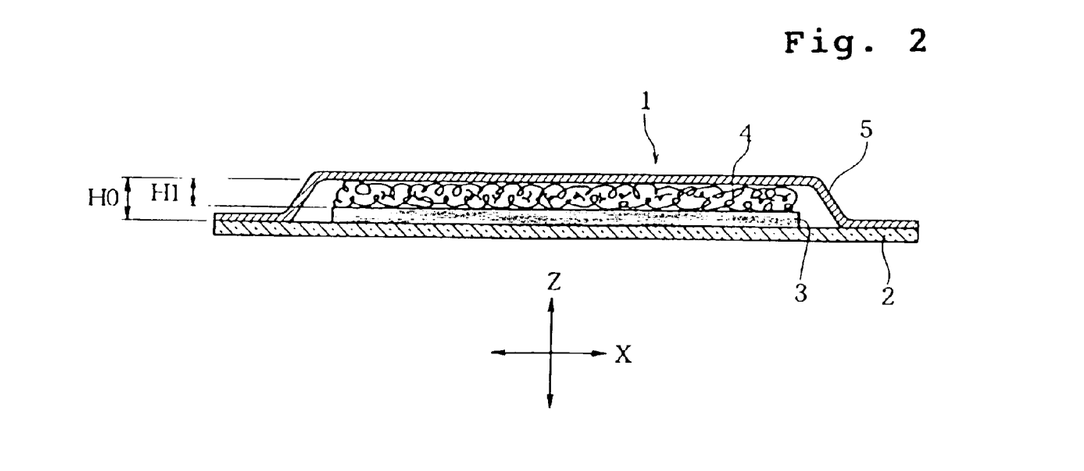
FIG. 2 is a widthwise sectional view of the sanitary napkin taken along line II—II of FIG. 1.
Figure 3:
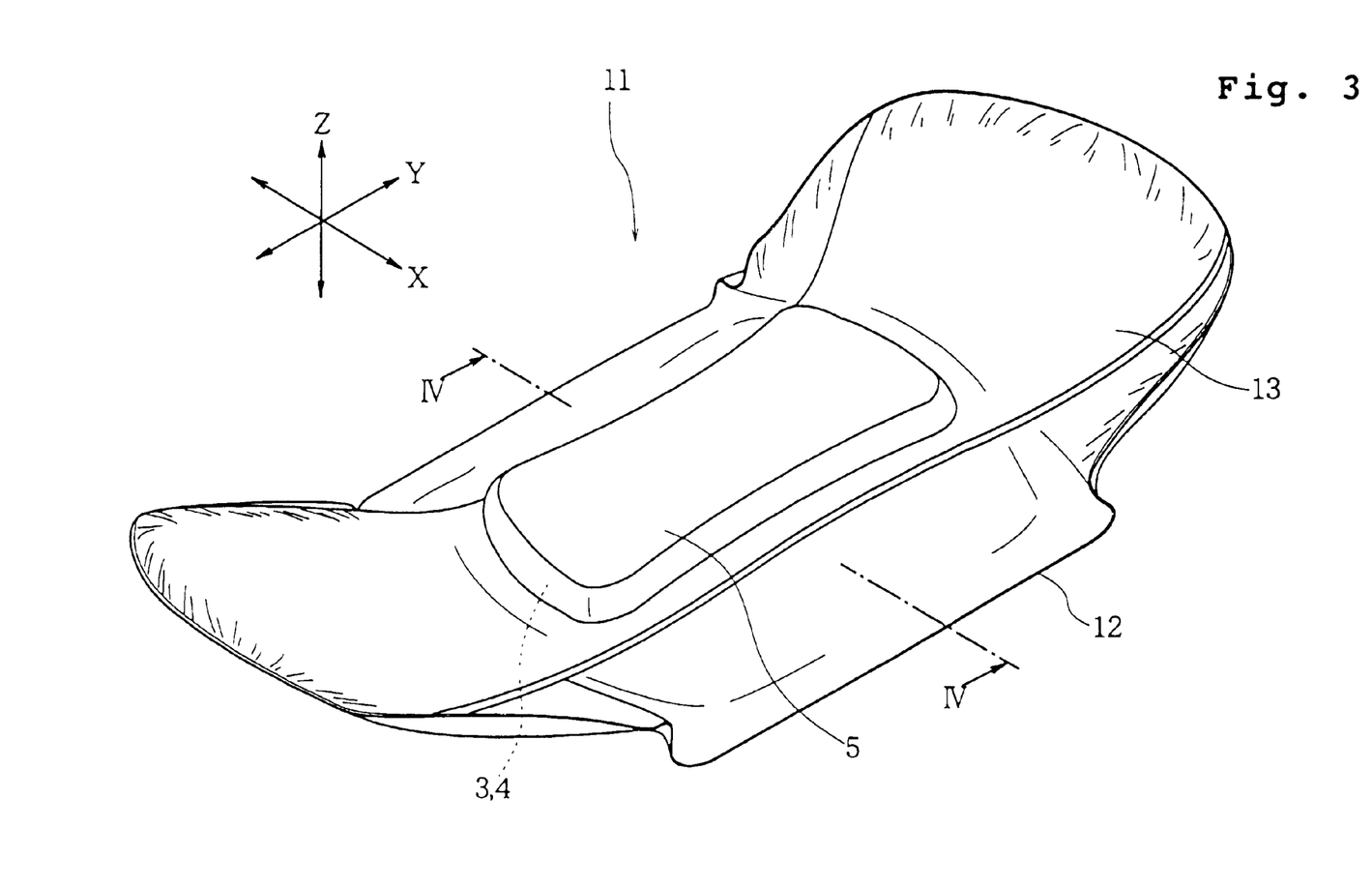
FIG. 3 is a perspective view showing another embodiment of the sanitary napkin.
Figure 4:
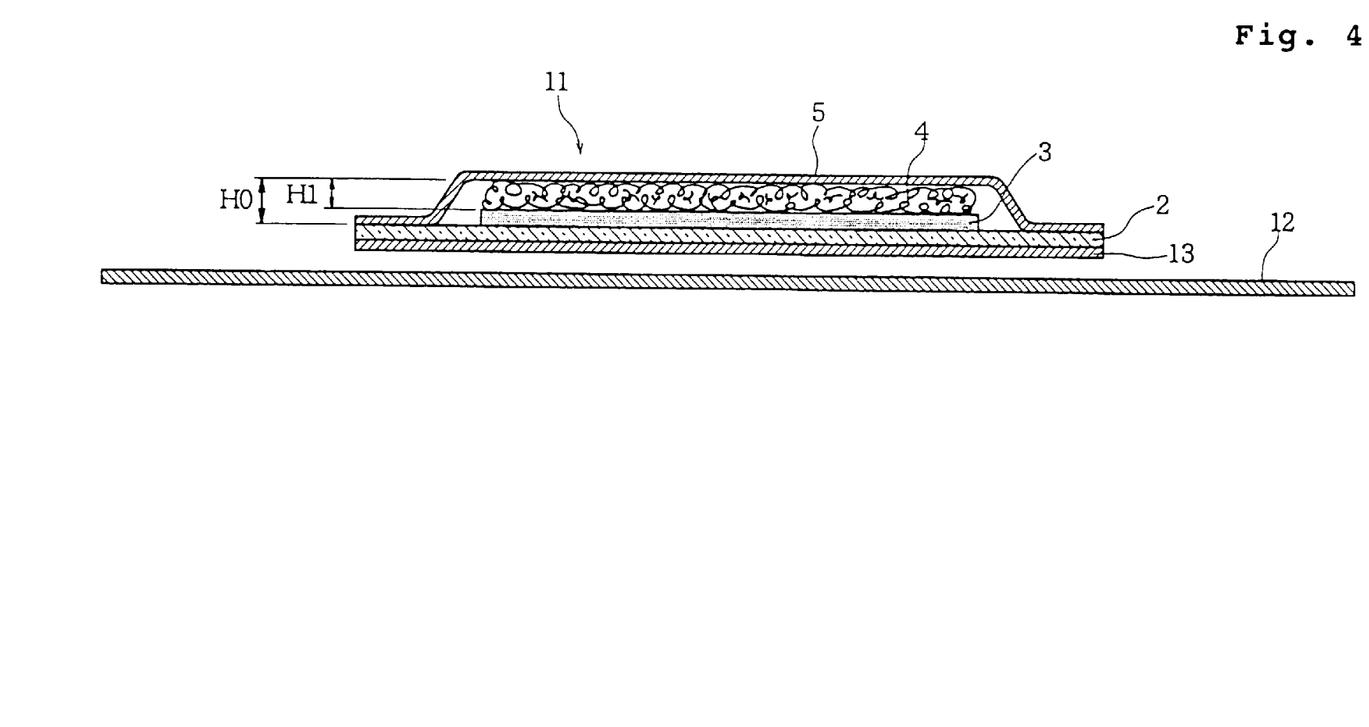
FIG. 4 is a sectional view taken along line IV—IV of FIG. 3.
Figure 5A:
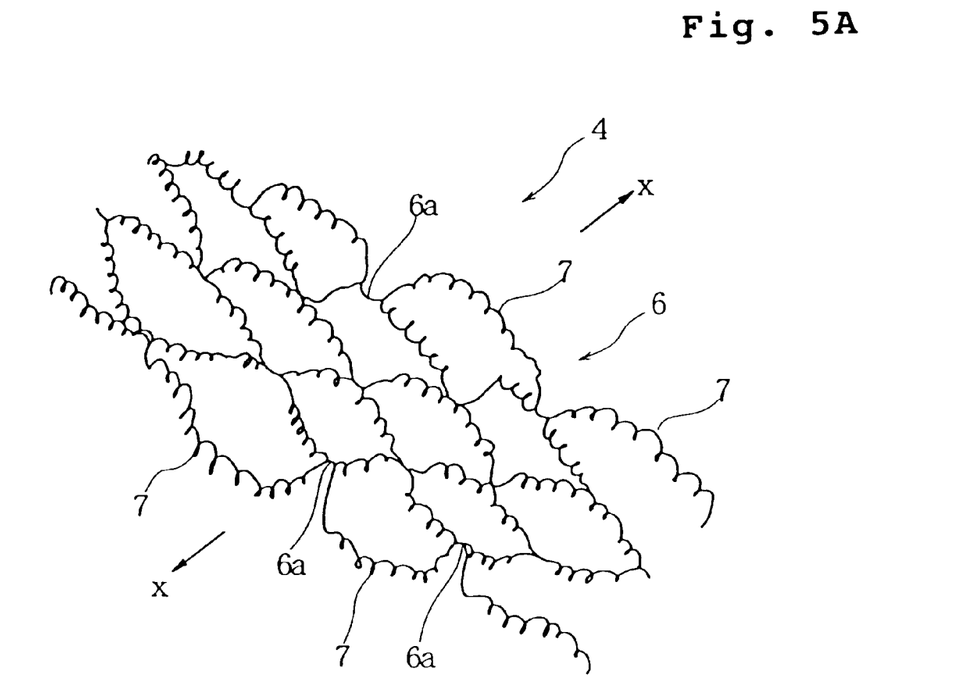
FIG. 5A is an enlarged perspective view showing a portion of a network sheet prepared by splitting a film.
Figure 5B:
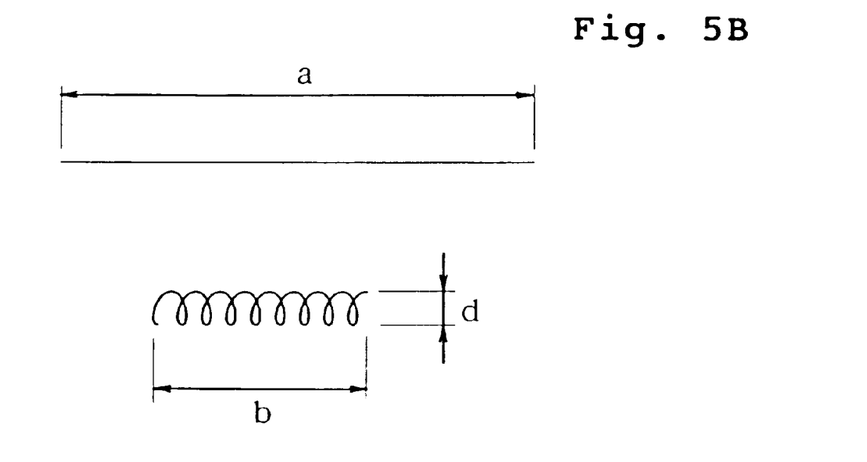
FIG. 5B is an explanatory view of a crimped fiber.
Figure 6:
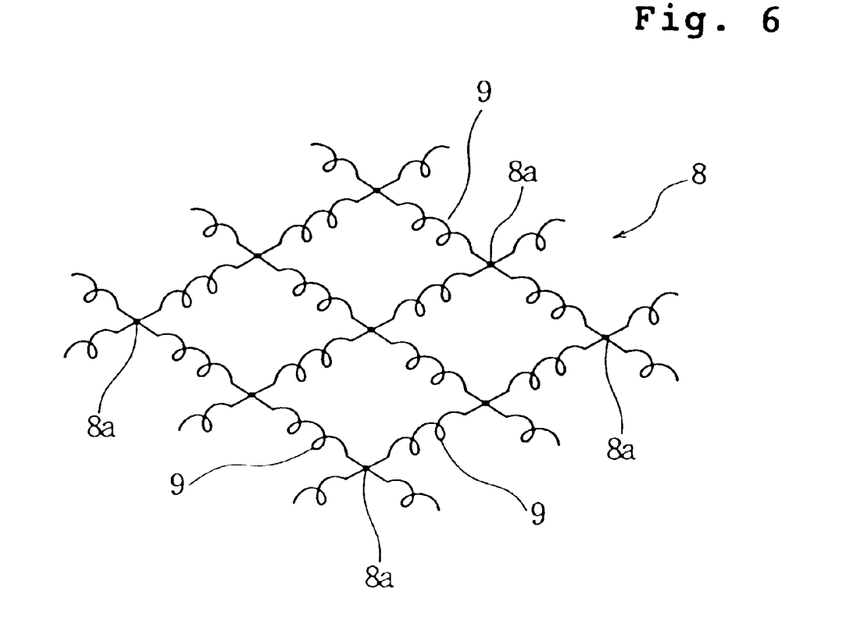
FIG. 6 is an enlarged perspective view showing a portion of a network sheet prepared by joining crimped fibers at their intersections.

FIG. 1 is a perspective view showing a sanitary napkin as an absorbent article according to an embodiment of the invention; FIG. 2 is a widthwise sectional view of the sanitary napkin taken along line II—II of FIG. 1; FIG. 3 is a perspective view showing another embodiment of the sanitary napkin; FIG. 4 is a sectional view taken along line IV—IV of FIG. 3; FIG. 5A is an enlarged perspective view showing a portion of a network sheet of crimped fibers; FIG. 5B is an explanatory view of a crimped fiber; and FIG. 6 is an enlarged perspective view showing a portion of another network sheet of crimped fibers.

A sanitary napkin 1, as shown in FIGS. 1 and 2, has four layers. As a first layer (i.e., a lowermost layer), there is provided a liquid-impermeable back sheet 2 acting as a support sheet. As a second layer over the back sheet 2, there is provided an absorbent core 3 acting as a liquid-absorbing layer. As a third layer over the second layer, there is provided a liquid-permeable layer (i.e., a crimped fiber layer) 4 which is formed of crimped fibers. As a fourth layer (i.e., an uppermost layer) over the liquid-permeable layer 4, there is provided a liquid-permeable surface sheet 5. The back sheet 2 and the surface sheet 5 are joined to each other outside of the periphery of the absorbent core 3.

The back sheet 2 may be made of an air-permeable PE (polyethylene) film, a liquid-impermeable or hydrophobic nonwoven fabric or a laminated material of a nonwoven fabric and a film, for example. The absorbent core 3 may be made of a web of liquid-absorbing fibers such as pulp, a layer of highly water-absorbent polymer in the form of granules or fibers, or laminate of liquid-permeable sheets such as tissue or nonwoven fabric, for example. The fiber web or the highly water-absorbent polymer layer may be enveloped by a liquid-permeable sheet such as tissue. In addition, it is possible to incorporate with the fiber web the highly water-absorbent polymer.

The surface sheet 5 may be made of a liquid-permeable nonwoven fabric (e.g., a spun-bonded nonwoven fabric, a point-bonded nonwoven fabric or a spun-laced nonwoven fabric) or a porous film. They are preferably hydrophobic.

A sanitary napkin 11, as shown in FIGS. 3 and 4, includes a laminate having substantially the same structure as that of the sanitary napkin 1. More specifically, the laminate is constructed to include the back sheet (or support sheet) 2, the absorbent core 3, the liquid-permeable, crimped fiber layer 4, and the surface sheet 5. This laminate is provided on a stretchable sheet 13. The stretchable sheet 13 is joined, at its two end portions lying opposite one another in the longitudinal direction thereof, to a base sheet 12 to be worn on an external wear such as shorts.

The stretchable sheet 13 may be made of a stretchable film, a urethane foam, a melt-blown nonwoven fabric of an elastomer resin, a nonwoven fabric of stretchable shrink fibers, or a rubber sheet, for example.

In the sanitary napkin 11 shown in FIGS. 3 and 4, the base sheet 12 is applied to the external wear such as the shorts so that the surface sheet 5 over the absorbent core 3 comes into close contact with the vaginal opening. At this time, the base sheet 12 and the absorbent core 3 can move relatively independently of each other to prevent displacement between the absorbent core 3 and the vaginal opening and twist of the absorbent core 3, as might otherwise be caused by the motions of the wearer's body.

In the embodiments shown in FIGS. 2 and 4, the total thickness H0 of the absorbent core 3 and the liquid-permeable layer 4 is preferably 5 to 50 mm and more preferably 10 to 30 mm. The thickness H1 of the liquid-permeable layer 4 is preferably 3 to 30 mm and more preferably 10 to 25 mm. With the sizes H0 and H1 being with the above-specified ranges, there can be provided an improved fit to the uneven surface of female private part, so that even the laminate of the back sheet 2, the absorbent core 3, the liquid-permeable layer 4 and the surface sheet 5, which is separated from the base sheet 12 as shown in FIGS. 3 and 4, can be brought into close contact with the vaginal opening while conforming to the uneven surface thereof.

As shown in FIG. 5A and FIG. 6, the liquid-permeable layer 4 is an aggregate (or cluster) of crimped fibers. More specifically, the liquid-permeable layer 4 is a network sheet 6 or 8, in which crimped fibers 7 or 9 are interconnected into a network. The crimped fibers for use in the liquid-permeable layer 4 will be discussed below with reference to FIG. 5B.

As shown in FIG. 5B, the term "crimped fiber" as used herein refers to a fiber that is shrunk from its original length "a" to a length "b" by deforming it into a three-dimensional helical shape or the like to have a crimping external diameter (e.g., helical external diameter) "d". The force in the fiber longitudinal direction necessary for returning the length "b" to the length "a" can be remarkably low. The crimped fiber has a remarkably low elastic modulus in the direction of the crimping external diameter "d". In other words, the external force necessary for crushing the crimping external diameter "d" is low, and the repulsive force for recovery is low, but the recovery properties to recover to the crimping external diameter "d" when the external force is removed is excellent.

Therefore, in the case where the crimped fibers are arranged to extend generally along the liquid-receiving face of the absorbent core 3 (i.e., along the X-Y plane) so that the crimping external diameter "d" thereof is directed generally in the height direction (i.e., in the Z direction) from the core surface, the liquid-permeable layer 4 can be easily bent in accordance with the sanitary napkin 1 or 11 being bent in the longitudinal direction (i.e., Y direction) or in the transverse direction (i.e., X direction) thereof. At this time, moreover, the liquid-permeable layer 4 does not apply an excessive restoring force for the flat state to the sanitary napkin 1 or 11 in its entirety.

When the surface sheet 5 is pushed from the liquid-receiving side, on the other hand, the liquid-permeable layer 4 is compressed and deformed in the height direction so that the surface sheet 5 easily comes into close contact with the vaginal opening while conforming to the unevenness thereof.

Since the crimping external diameter "d" is directed generally in the height direction (i.e., in the Z direction), moreover, the crimped portions of the fibers function to guide the body liquid having passed through the surface sheet 5, quickly into the absorbent core 3. Still moreover, the liquid-permeable layer 4 has a high percentage of voids so that it can quickly guide the body liquid into the absorbent core 3 even when the crimped fibers are made of a hydrophobic resin having no hydrophilic property. It should be noted that the crimped fibers thus made of a hydrophobic resin may be treated to be hydrophilic.

In order to exhibit the aforementioned function, the crimped fibers are preferably given such a sectional shape as has a larger width of 10 to 500 microns than a thickness of 10 to 100 microns. In addition, the crimped fibers preferably have the maximum crimping external diameter "d" of 0.3 to 20 mm in a free state without any external force.

The network sheet 6 of FIG. 5A is prepared by co-extruding resins of different MFRs (Melt Flow Rates), (i.e., a highly extensible resin of a low MFR and a non-extensible resin of a high MFR) into two layers to form a laminated film, and by softening the laminated film at a lower temperature of 80 to 150° C. than its melting point and monoaxially stretching the softened film in its flow direction to orient the film in that flow direction. The film thus oriented is cut (or split) in the X direction by a fibrillating machine so that it may be torn into separate fibers while leaving the connections 6a partially. In the fibers thus separated, a crimp is enabled to develop by the difference in the MFRs of the two sides to produce the crimped fibers 7 which are interconnected at the connections 6a to form a network. In this network, large voids are formed between the crimped fibers.

On the other hand, the network sheet 8 of FIG. 6 is prepared by arranging crimped long fibers 9, which are made of a thermoplastic material and crimped in advance, at a constant spacing (e.g., 5 to 50 mm) two-dimensionally, and by fusing and interconnecting the crimped fibers 9 at their intersections (or junction points) 8a into a network. In order to crimp those long fibers, there may be adopted any suitable methods known in the art, including: a method of developing the crimps by making the fibers sectionally heterogeneous and by heating them or treating them with hot water; a method of passing and pressing the fibers between heated gears; a method of twisting (or winding) the fibers temporarily and setting the twisted fibers thermally; and a method of forcing the filaments into a box by a hot air jet to bend the filaments.

Examples of the thermoplastic material for forming the crimped fibers 7 of FIG. 5A and the crimped fibers 9 of FIG. 6, include a homogeneous PP (polypropylene) resin, a block PP (polypropylene) resin, a high-density PE (polyethylene) resin, and the like.

The aforementioned liquid-permeable layer 4 is formed by using a single layer of the network sheet 6 or 8, or by stacking multiple layers of the network sheet 6 or 8.

Figure 7:
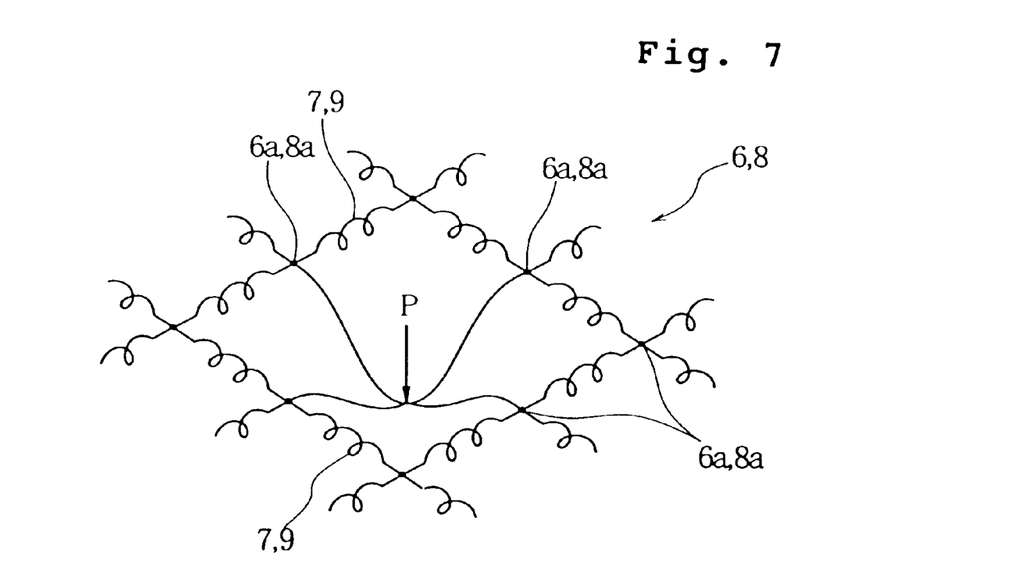
FIG. 7 is a perspective view showing the state in which a pushing force is applied to the network sheet.

The network sheet 6 or 8 is enabled to stretch sufficiently freely in the individual directions, because the fibers are crimped between adjacent connections 6a or between adjacent junction points (or intersections) 8a. Moreover, where a pushing force P is applied to a portion of the network sheet 6 or 8, as shown in FIG. 7, the pushing force P is absorbed by the crimped fibers being extended at the pushed portions. Therefore, only a portion is compressed, when pushed, in its thickness direction, but the compression is not propagated to other portions. Thus, the liquid-permeable layer 4 formed of the network sheet 6 or 8 takes a visco-elasticity.

In order to exhibit that character, it is preferable that the shrinking tension for a width of 25 mm is 50 mN or less when a tensile strain of 50% is applied in the longitudinal direction of the absorbent article to the layer (or the liquid-permeable layer 4) of the network sheet 6 or 8 having a thickness of 3 to 30 mm, from the free state in which no external force is applied.

The percentage of voids (i.e., the ratio of voids to a unit volume) of the liquid-permeable layer 4 made of the network sheet 6 or 8 is preferably within a range of 97.9 to 99.9%. Below the percentage of voids of 97.9%, the crimped fibers 7 or 9 have a less crimping degree and a less compressive deformation so that it is difficult to conform to the shape of the vaginal opening and therearound. In addition, the permeability of the liquid having passed through the surface sheet 5 into the absorbent core 3 is deteriorated. Over the percentage of voids of 99.9%, on the other hand, less crimped fibers are directed in the height direction between the surface sheet 5 and the absorbent core 3 to deteriorate the function to draw the body liquid from the surface sheet 5 to the absorbent core 3. More preferably, the percentage of voids is in a range of 98.4 to 99.1%. The fiber density of the liquid-permeable layer 4 for realizing the more preferable range is expressed by 0.006 to 0.015 $g/cm^3$.

The liquid-permeable layer 4 having the above-specified percentage of voids is so bulky and highly voluminous that it can provide a soft, gentle feel to the wearer's body. On the other hand, the liquid-permeable layer 4 has high recovery properties and hardly goes out of shape. When the sanitary napkin 1 or 11 is worn on the crotch of a female, therefore, it can exhibit high contact and seal for the complicated uneven surface shape of the female private part. For example, the surface sheet 5 can retain a contact of 90% or more so that it can absorb the menstrual blood discharged from the vaginal opening, positively to prevent the leakage.

In the invention, if desired, the absorbent core 3 and the liquid-permeable layer 4 may be integrated to be a single layer by interspersing particulates of a liquid-absorbent material (i.e., particulated liquid-absorbent materials) among the crimped fibers 7 or 9 of the network sheet 6 or 8 having a high void percentage (i.e., by burying particulated liquid-absorbent materials in the voids of the network sheet 6 or 8). In this case, the manufacture cost can be lowered. The "particulates" refers to a liquid-absorbent material in any form, shape, or size including but not limited to powders, pellets, grains, discrete length fibers, or the like. For example, the particulated liquid-absorbent materials include pulp, highly water-absorbent polymer in the form of granules or fibers, or combinations thereof. The resulting layer having the absorbent core 3 and the liquid-permeable layer 4 integrated may be enveloped by a liquid-permeable sheet such as tissue. Of course, it is also possible to provide such a layer over the absorbent core 3.

Here will be described an example of the sanitary napkin 1.

EXAMPLE

Network sheets of crimped fibers of Samples 1, 2, 3, 4 and 5 were each manufactured by co-extruding a resin (for upper layer) at a stretch grade of a low MFR (melt flow rate) and a resin (for lower layer) at a non-stretch grade of a high MFR to form a laminated film, by softening the film at temperature of 80 to 150° C. and monoaxially stretching the softened film in its flow direction to orient the film, and by splitting the oriented film by a fibrillating machine. The developabilities on the crimp were examined, and their results are enumerated in Table 1.

TABLE 1

| Samples | Upper Layer | Lower Layer | MFR (Upper/ Lower) (g/10 mins.) | Thickness (Upper/ Lower) (microns) | Crimp Developed |
|---|---|---|---|---|---|
| 1 | Homo-PP | Homo-PP | 0.5/2.4 | 20/20 | Good |
| 2 | Homo-PP | Homo-PP | 0.5/6.5 | 20/20 | Very Good |
| 3 | Homo-PP | Homo-PP | 2.4/6.5 | 20/20 | Bad |
| 4 | Block-PP | Block-PP | 0.5/5.0 | 20/20 | Very Good |
| 5 | High-Density-PP | Low-Density-PP | 0.7/1.6 | 20/20 | Good |

Next, various tests were made using Samples 1 and 2, from h the satisfactory results were obtained on the crimp developability. Here will be explained those tests.
(1) Specifications of Prior Art and Samples
(Specifications of Prior Art)
"Body Fit R" manufactured by Uni-Charm Corporation was as the commercially available sanitary napkin.
(Specifications of Samples)
Surface Sheet: an air-through nonwoven fabric or an apertured PE film
Absorbent Core: granular SAP (superabsorbent polymer) or fibrous SAP
Back Sheet: a PE film
Network Sheet: Sample 1 and Sample 2
Detail of the crimped fibers is enumerated in Table 2.

TABLE 2

| | Thickness (microns) | Width (microns) | Helical Ext. Diameter (mm) | Density (g/cm$^3$) | Void % | Bulk (mm) | Weight (g/m$^2$) |
|---|---|---|---|---|---|---|---|
| Sample 1 | 40 | 170 | 3 | 0.014 | 98.5 | 11.5 | 130 |
| Sample 2 | 40 | 170 | 3 | 0.007 | 99.2 | 23 | 130 |

Figure 8:
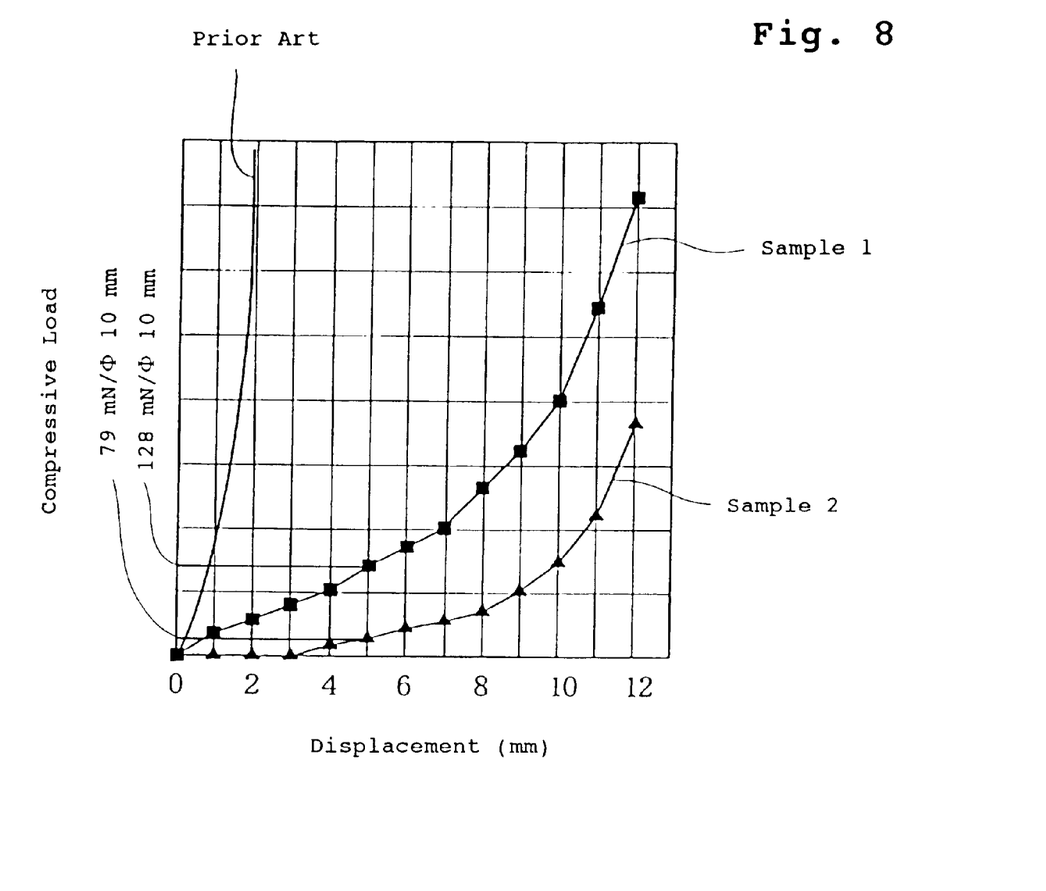
FIG. 8 is a graph plotting the measured results of compressive loads against a displacement when a load was applied to the surface of the sanitary napkin.

(2) Tests on Compression Resistances
(Testing Method)
According to the KES compression characteristic measurements, the end face of a diameter of Φ=10 mm was vertically pushed onto the surface sheet 5 of the sanitary napkin, and the compressive loads (mN/Φ of 10 mm) for the displacement of the surface sheet 5 were measured on Prior Art, Sample 1 and Sample 2.
Here, the pushing speed of the KES compression tester was 0.1 cm/sec.
(Measured Results)
FIG. 8 is a graph plotting the measured results of compressive loads against a displacement when a load was applied to the surface of the sanitary napkin.
As seen from FIG. 8, it can be confirmed that a compressive load over 500 mN/Φ of 10 mm was required for Prior Art to push the end face of the diameter of Φ=10 mm by 5 mm whereas a load of about 128 mN/Φ of 10 mm was sufficient for Sample 1 and a load of about 79 mN/Φ of 10 mm was sufficient for Sample 2.

Therefore, it is found that the present sanitary napkins can establish a large displacement with a compressive load of 150 mN/Φ of 10 mm or less so that it is more excellent in softness.
(3) Wearing Tests
The measured results on the wearing fitness are tabulated for Prior art, Sample 1 and Sample 2.

TABLE 3

| | Contact at Crotch | Physical Disorder |
|---|---|---|
| Prior Art | 54% | YES |
| Sample 1 | 85% | NO |
| Sample 2 | 83% | NO |

As enumerated in Table 3, it could be said that the present sanitary napkins (i.e., Samples 1 and 2) enjoy a higher contact (or fitness) with the female private part than that of Prior art and give little physical disorder while being worn. In other words, it is found that the present sanitary napkins are sufficiently deformable but less stimulant to the skin.
(4) Tests on Evaluations of Liquid Absorbency
Tests were made on the infiltration, diffusivity and liquid returnability under pressure by attaching 0.7% of hydrophilic oil to Samples 1 and 2.
Here, the hydrophilic oil used was a surface active agent composed mainly of sulfonic acid.
(Liquid Used)
U/C Artificial Menstrual Blood (i.e., an aqueous solution containing glycerin or the like in 1 litter of ion-exchange water)
(Infiltration Time)
The artificial menstrual blood was injected into the surface sheet 5 firstly by 3 cc/sec. and secondly by 4 cc/sec. Then the time period for which the injected blood was absorbed by the inside of the sanitary napkin and disappeared from the surface sheet 5, was measured as the infiltration time (secs.).
(Diffusivity)
After 7 cc/min. of artificial menstrual blood was injected and left for 1 min., the longitudinal and transverse sizes (in dia. mm) of the liquid in the surface and back of the absorbent core were compared.
(Liquid Returnability (Rewet-Back) under Pressure)
7 cc/min. of artificial menstrual blood was left for 1 min., after injected, and filter paper was then placed on the surface of the evaluation sample and subjected to a pressure of 3,430 Pa. The applied pressure was released after 3 mins., and the quantity of the liquid absorbed by the filter paper placed on the sample surface was measured. At this time, there were compared the indications of percentages of the liquid weight (i.e., the rewet-back) of the artificial menstrual blood having exuded onto the surface sheet 5. Specifically, this percentage was determined from the Formula:

Liquid Returnability (%) under Pressure=(Quantity of Liquid Absorbed by Filter Paper)/(7 cc/min. of Artificial Menstrual Blood)×100.

(Measured Results)

The measured results are enumerated in Table 4.

TABLE 4

|  | Infiltraion Time | | Diffusivity (mm) | | Return- |
|---|---|---|---|---|---|
|  | 1st (secs.) | 2nd (secs.) | Surface | Back | ability (%) |
| Prior Art | 2.5 | 4.6 | 25 | 43 | 34.3 |
| Sample 1 | 2.3 | 3.1 | 5 | 10 | 10.3 |
| Sample 2 | 2.5 | 3.5 | 7 | 11 | 15.4 |

It can be confirmed from Table 4 that the diffusivity could be suppressed more than Prior art and that the infiltration time and the liquid returnability under pressure could be improved. From these, it is found that the liquid-permeable layer 4 is excellent in the permeability of the liquid such as the artificial menstrual blood.

(5) Test on Recovery Percentage of Network Sheet of Crimped Fibers (Testing Method)

The recovery percentage (A/B×100) was determined between the thickness (A) of the network sheet after the compression pressure of 4,900 Pa was applied in an oven of 40° C. for 10 mins. and the thickness (B) of the network sheet before loaded.

(Measured Results)

Sample 1:66.7%.

From this result, it is confirmed that the network sheet has a recovery percentage within a range of about 40 to 80%.

According to the invention thus far described, the liquid-permeable layer of the crimped fibers, which is provided under the surface sheet, can reduce the pressing feel on the wearer's body. In addition, the liquid-permeable layer can improve fitness to thereby prevent the leakage of the discharged liquid.

Moreover, the liquid-permeable layer can provide improved bulkiness so that the absorbent article such as a sanitary napkin can be soft and gentle to the skin.

Although various exemplary embodiments have been shown and described, the invention is not limited to the embodiments shown. Therefore, the scope of the invention is intended to be limited solely by the scope of the claims that follow.

What is claimed is:

1. An absorbent article comprising:

a support sheet;

a liquid-absorbing layer disposed on said support sheet; and a liquid-permeable surface sheet covering a liquid-receiving face of said liquid-absorbing layer, wherein between said liquid-absorbing layer and said surface sheet, there is provided a liquid-permeable crimped fiber layer of crimped fibers which remain in a crimped state without a presence of any external forces, the crimped fiber layer being formed by interconnecting said crimped fibers to leave voids therebetween, and a pushing load necessary for pushing said surface sheet by 5 mm is 150 mN or less for an area having a diameter of 10 mm for a laminate of said liquid-absorbing layer, said liquid-permeable layer and said surface sheet.

2. The absorbent article as set forth in claim 1, wherein said crimped fiber layer is prepared by laminating a plurality of resin layers of different MFRS (melt flow rates) into a laminate film and by splitting the laminate film into a network.

3. The absorbent article as set forth in claim 1, wherein said crimped fiber layer is prepared by joining said crimped fibers at point where said crimped fibers intersect to formed a network of fibers.

4. The absorbent article as set forth in claim 1, wherein said crimped fibers have a sectional shape with a larger major axis of 10 to 500 microns than a minor axis of 10 to 100 microns and a maximum crimping external diameter of from 0.3 to 20 mm in a free state without any external force being applied thereto.

5. The absorbent article as set forth in claim 1, wherein a bulk recovery percentage of a pushed portion when a pushing force or 5 mm is released is no less than 40% and no more than 100%.

* * * * *